United States Patent [19]
Ligtenberg et al.

[11] Patent Number: 4,722,348
[45] Date of Patent: Feb. 2, 1988

[54] CATHETER TIP PRESSURE TRANSDUCER

[75] Inventors: Hendrikus C. G. Ligtenberg, Nietap; Jozef G. M. Leuveld, Leek, both of Netherlands

[73] Assignee: Sentron v.o.f., Roden, Netherlands

[21] Appl. No.: 907,073

[22] Filed: Sep. 12, 1986

[30] Foreign Application Priority Data

Sep. 17, 1985 [NL] Netherlands ............................ 8502543

[51] Int. Cl.4 ................................................. A61B 5/02
[52] U.S. Cl. ..................................... 128/675; 128/748; 73/726
[58] Field of Search ................................ 128/672–675, 128/748; 73/720–721, 726–727, 777

[56] References Cited

U.S. PATENT DOCUMENTS 3,724,274  4/1973  Millar ............................... 128/675 X
4,023,562  5/1977  Hynecek et al. ................ 128/675 X
4,274,423  6/1981  Mizuno et al. ...................... 128/675
4,456,013  6/1984  De Rossi et al. .................... 128/675

FOREIGN PATENT DOCUMENTS 8302952  3/1985  Netherlands ........................ 128/675

Primary Examiner—Kyle L. Howell
Assistant Examiner—Angela D. Sykes
Attorney, Agent, or Firm—Tarolli, Sundheim & Covell

[57] ABSTRACT

A catheter tip pressure transducer is employed for purposes of measuring fluid pressure within a living body. This includes a tubular housing having a pressure inlet aperture therein. A semiconductor block is carried within the housing and has first and second oppositely facing surfaces, one of which faces the inlet aperture and the other faces in the opposite direction. One of the surfaces has a recess formed therein of such a depth to define an elongated rectangular shaped membrane. A pair of elongated grooves are formed in the nonrecessed surface of the semiconductor block. These grooves are in registry with and straddle the longitudinal side edges of the membrane and define therebetween a raised longitudinally extending central portion in the form of a membrane beam which acts as a free beam supported at its opposite ends by the semiconductor block. Pressure forces acting on the membrane beam result mainly in longitudinally extending deformation of the beam and this is sensed by one or more strain gauges carried by the beam. By this construction, the cross sectional dimensions are optimized so that the transducer may be mounted in catheters and needles of smaller internal diameters.

8 Claims, 11 Drawing Figures

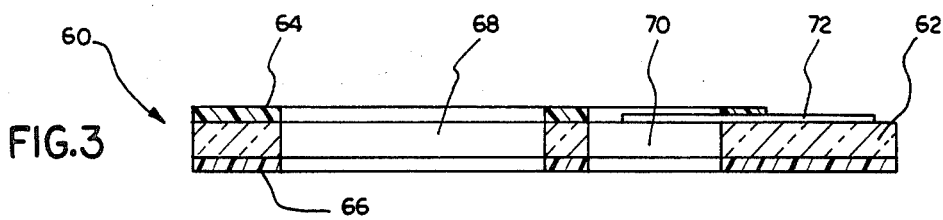
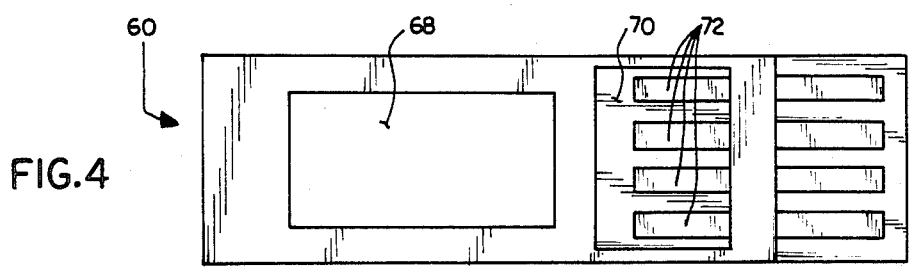
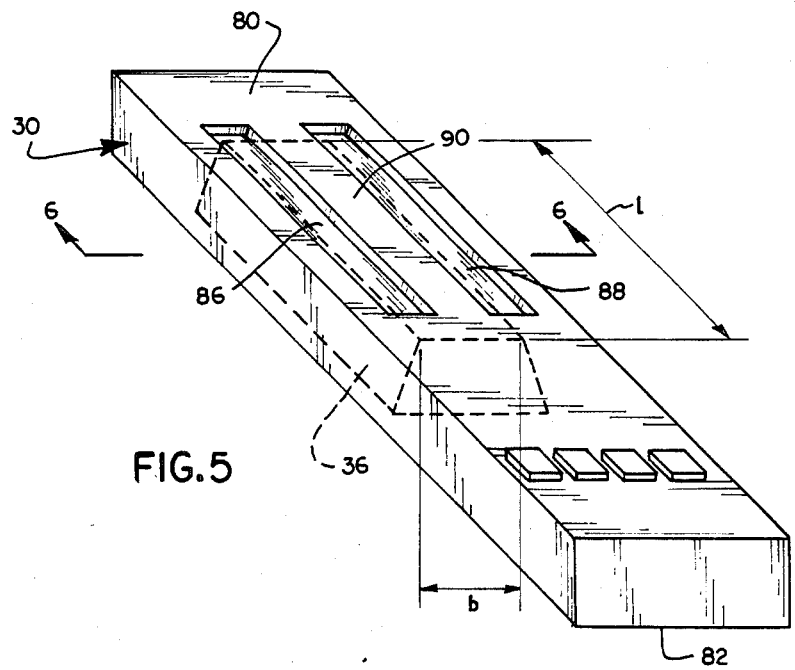
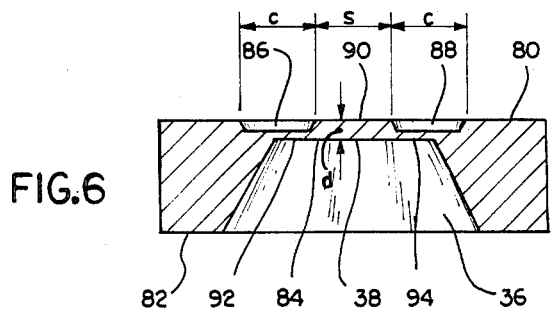

CATHETER TIP PRESSURE TRANSDUCER

BACKGROUND OF THE INVENTION

This invention relates to the art of pressure sensors and, more particularly, to a catheter tip pressure transducer of sufficiently small size that it may be employed for measuring fluid pressure, such as blood pressure, within the human body.

Although the invention will be described in detail herein with respect to its employment in measuring blood pressure, it is to be appreciated that the pressure transducer may be employed within a hollow needle for use in measuring pressure at remote locations requiring transducers of exceedingly small size, i.e., of a size sufficiently small that it can be inserted into a blood vessel or the like.

Catheters have been used in the art for monitoring variations in blood pressure within a blood vessel, such as within the cardiovascular system. Such catheters include those employing catheter tip transducers insertable into a blood vessel with the transducer providing direct pressure monitoring by transducing blood pressure at the region of interest. Such a catheter tip transducer may employ semiconductor material constructed and arranged with resistors and the like for use in developing an electrical signal representative of the monitored pressure and transmitting the signal by electrical conductors through the length of the catheter to meters or the like located externally of the body being tested.

An example of such a catheter tip pressure transducer is found in the Mizuno et al., U.S. Pat. No. 4,274,423. The transducer disclosed there includes a pressure sensor disposed within the end portion of a catheter. The pressure sensor takes the form of a pressure sensitive diaphragm constructed from a block of semiconductor material, such as silicon. The diaphragm is located adjacent a side port in a housing connected to the end of the catheter with the side port providing access to the pressure medium. The diaphragm is deflected in dependence upon the pressure and the deflection is sensed by one or more strain gauges located in the diaphragm. The strain gauges are connected by suitable conductors to a meter located outside of the catheter.

A major concern with such catheter tip pressure transducers is to provide a transducer which is sufficiently small so as to be employed in a catheter adapted to be inserted into a blood vessel of a patient, while also being sufficiently responsive to pressure variations to provide meaningful electrical output signals. For example, the preferred outside diameter of such a catheter may be on the order of 2 or 3 millimeters. Consequently, the cross sectional dimensions of a pressure sensor of the type employing a membrane or diaphragm as discussed above must be optimally small. The semiconductor block containing the diaphragm or membrane of the type employed in Mizuno may well have a width on the order of 1.2 millimeters, which limits the size of the catheter and, hence, its application for use in measuring blood pressure within a blood vessel.

It is, therefore, a primary object to provide a catheter tip pressure transducer exhibiting cross sectional dimensions which are reduced over that of the prior art without impairing its operation.

To achieve the foregoing objective in accordance with the present invention, the catheter tip pressure transducer includes a tubular housing having a pressure inlet aperture proximate to one end thereof. An elongated block of semiconductor material is mounted within the housing and has first and second oppositely facing surfaces, one of which faces the inlet aperture. The block has a rectangular recess located in the first surface. The floor of the recess together with the second surface define a relatively thin rectangular flat portion having a length l and a width b and a thickness d. A pair of longitudinally extending grooves are formed in the flat portion of one of the surfaces thereof at a location corresponding with the longitudinal edges of the rectangular flat portion. This leaves an elongated rectangular membrane beam of a width s and a length l and a thickness d supported at its free ends by the semiconductor block and relatively unsupported along its longitudinal edges. The amount of strain in the beam in response to applied pressure is mainly determined in the length and the thickness of the beam and relatively not by the width allowing the width to be small without impairing sensitivity. At least one strain gauge is mounted on the beam, which serves as a deformable membrane for providing electrical signals by way of suitable electrical connecting means through the catheter to a meter or the like located externally thereof.

In accordance with another aspect of the present invention, the longitudinally extending grooves bordering the membrane beam extend through the rectangular portion defining two elongated openings or slots along the longitudinal side edges of the beam.

In accordance with a still further aspect of the present invention, the openings along the longitudinal side edges of the beam are closed with a thin layer of polymer permitting a pressure differential to exist across the oppositely facing surfaces of the beam.

BRIEF DESCRIPTION OF THE DRAWINGS

The foregoing and other advantages of the invention will become more readily apparent from the following description of the invention as taken in conjunction with the accompanying drawings which are a part hereof and wherein:

FIG. 3 is an enlarged view, partly in section, of a connector tape employed in FIG. 2;

FIG. 4 is a plan view of the tape shown in FIG. 3;

FIG. 5 is a perspective view of a pressure-responsive element employed in the embodiment of FIG. 2;

FIG. 6 is a sectional view taken along line 6—6 looking in the direction of the arrows in FIG. 5;

DETAILED DESCRIPTION OF PREFERRED EMBODIMENT

Figure 1:
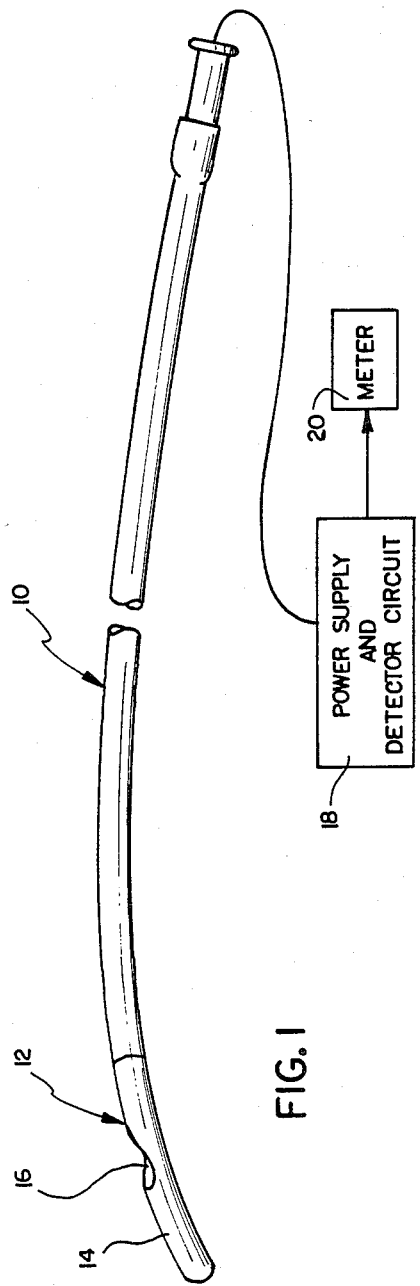
FIG. 1 is a schematic illustration showing one application of the invention in the form of a catheter tip transducer mounted on the distal end of a catheter for use in monitoring blood pressure or the like in a living body.

Reference is now made to the drawings wherein the showings are for purposes of illustrating a preferred embodiment only, and not for limiting same. FIG. 1 illustrates an application of the invention as applied to measurement of blood pressure within a blood vessel of a living body and includes an elongated, flexible, single lumen catheter 10 having a catheter tip pressure transducer 12, constructed in accordance with the present invention, secured to the catheter's distal end. As will be brought out in greater detail hereinafter, the catheter tip pressure transducer 12 includes a relatively rigid, tubular housing 14 having a side port pressure inlet aperture 16 therein for communicating blood pressure at the site of interest to a pressure responsive membrane located within the housing 14. This pressure responsive membrane deforms in dependence upon the pressure being monitored. This deformation is sensed by strain gauges in the form of piezoelectric resistors carried by the membrane and interconnected with electrical conductors which extend through the lumen of catheter 10 beyond the proximal end thereof to a suitable power supply and detector circuit 18.

As will be brought out in greater detail hereinafter, the strain gauges are connected in a Wheatstone bridge arrangement and any bridge imbalance representing the deformation of the membrane is detected by the detector circuitry and this may be recorded or otherwise read out, as with a suitable meter 20. In operation, the catheter 10 with the catheter tip pressure transducer is operative to be inserted within a blood-carrying vessel of a patient until the distal end is located at the site of interest to be monitored. With suitable power supplied, the pressure at the site of interest is then monitored by the detector circuitry and displayed or recorded, as with meter 20. The proximal end of the catheter permits atmospheric pressure to be supplied by way of the lumen within the catheter and this is communicated to the housing 14 in such a way that deformation of the membrane takes place with respect to atmospheric pressure.

Figure 2:
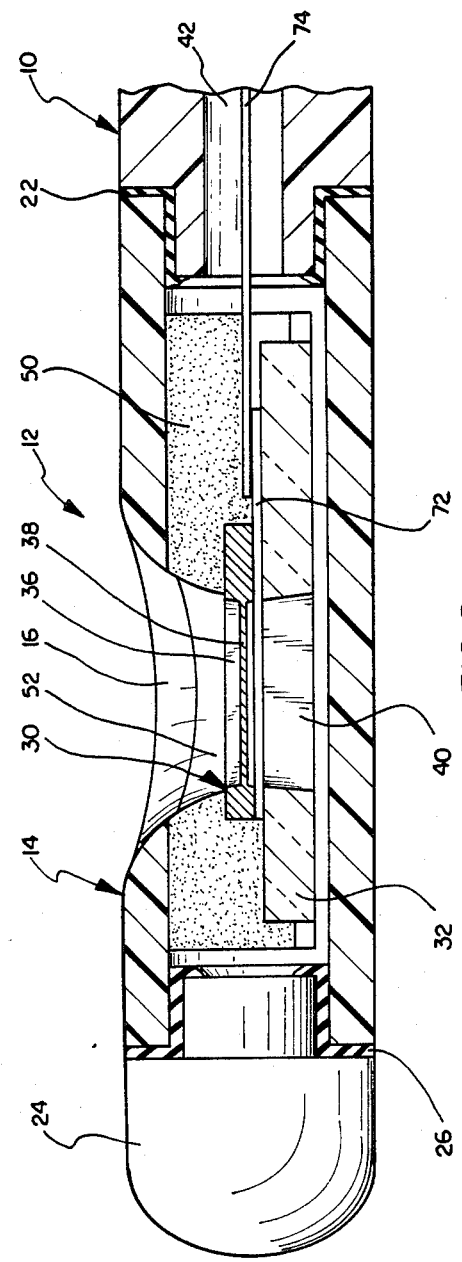
FIG. 2 is an enlarged, partially in section, view illustrating the catheter tip transducer.
Figure 7:
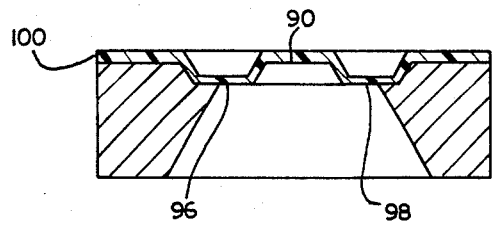
FIG. 7 is a view similar to that of FIG. 6 showing a second embodiment.

Reference is now made to FIG. 2, which illustrates the catheter tip pressure transducer in greater detail. As seen, the housing 14 may take the form of tubular structural member, which preferably is rigid relative to the catheter 10 with which it is secured to one end, as with a suitable epoxy 22 or the like. The opposite end of housing 14 may carry a suitable plug 24 secured to the housing 14, as with a suitable epoxy 26 or the like.

As previously discussed, the housing 14 is provided with a side port pressure inlet aperture 16 which extends through its side wall providing communication of pressure from a site of interest to the interior of housing 14. Within the housing there is provided a subassembly including a semiconductor block 30, made of silicon, carried by and in rigid connection with a rigid supporting member 32, which may be made of glass. The semiconductor block 30, to be described in greater detail hereinafter, has an elongated rectangular recess 36 defined in one face thereof and of such a depth that there remains a relatively thin diaphragm or membrane 38. The membrane 38 faces the inlet aperture 16 so that pressure variations in a blood vessel or the like may be communicated to the membrane. The membrane is responsive to the pressure and flexes or deforms as a result thereof.

The supporting member 32 is provided with an elongated rectangular opening 40 therethrough which is in registry with the rectangular-shaped membrane 38. The opening 40 is in communication with the lumen 42 within the catheter 10 so that atmospheric pressure may be communicated to the lower face (as seen in FIG. 2) of the membrane.

The semiconductor-supporting block assembly is held in place within housing 14 by means of a flexible adhesive 50, which secures the assembly to the inner walls of housing 14 in such a manner so as to permit atmospheric pressure communication between opening 40 in the supporting member 30 and the lumen 42 within catheter 10. Moreover, the adhesive 50 is provided with an aperture 52 in registry with the pressure inlet aperture 16 and the recess 36 for communicating pressure at the site of interest within the blood vessel or the like to the membrane 38.

The semiconductor block may be directly secured to the supporting member 32 by suitable means. Preferably, however, the semiconductor block and supporting member are coupled together by means of a tape used in the tape automatic bonding (TAB) process. Such a tape 60 is illustrated in FIGS. 3 and 4 and takes the form of an elongated rectangular tape composed of a three-piece laminate, including a central insulating layer 62 and oppositely facing adhesive layers 64 and 66. The adhesive layers 64 and 66 secure the semiconductor block 30 to the supporting member 32.

Tape 60 is also provided with a rectangular opening 68 corresponding in size and aligned in registry with the rectangular recess 36 in the semiconductor block as well as with the rectangular opening 40 in the supporting member 32. The tape has an additional opening 70 which is positioned so as to provide access to bonding pads located on the semiconductor block (to be described) so that they make electrical connection with electrical conductors 72 formed on pad 60. These electrical conductors 72 are, in turn, electrically connected to conductor members 74 which extend through the lumen of the catheter 10 throughout its length and thence to the power supply and detector circuit 18.

Reference is now made to FIGS. 5-8, which illustrate the semiconductor block 30 in greater detail. As shown in FIGS. 5 and 6, the semiconductor block 30 is an elongated rectangular structure made of silicon. The silicon has a (100) surface orientation. The block has oppositely directed major surfaces or faces 80 and 82. The elongated recess 36 is formed in face 82 and is of such a depth that the floor 84 of the recess defines, along with the oppositely directed face 80, a relatively thin rectangular-shaped membrane 38 of a thickness d. The rectangular-shaped recess 36 is formed in face 82 as by anisotropic etching known in the art, for example, by means of a KOH solution, such that the recess has a length l and a width b.

A pair of longitudinally extending grooves 86 and 88 are formed in the nonrecessed face 80, each having a depth extending more than ½ that of thickness d of the membrane and each of a width c. Each of these grooves is of a length l corresponding with the length of the membrane. Moreover, the grooves 86 and 88 are symmetrically located so as to equally straddle the longitudinally extending side edges of floor 84 in the recess 36. This is best illustrated in FIG. 6. The operating portion of the membrane is a raised central portion in the form of an elongated membrane beam 90 which is rigidly fixed at its opposite ends to the semiconductor block 30 in a longitudinal direction. In the lateral direction, membrane beam 90 is minimally connected to the semiconductor block by laterally extending web flanges 92 and 94, each of a width on the order ½c in the lateral direction. These web flanges provide essentially no lateral support and, hence, the membrane beam 90 acts as a free beam fixed at both ends. This may be carried out to its extreme, as in the embodiment of FIG. 7, by fully cutting through grooves 86 and 88 to define longitudinally extending slots 96 and 98. However, it is important to maintain a pressure differential between the oppositely directing faces of the membrane and, for this reason, the embodiment of FIG. 7 also includes a thin layer of polymer material 100 which covers face 80 and provides a thin lateral interconnection between the membrane beam 90 and the semiconductor block 30.

Figure 8:
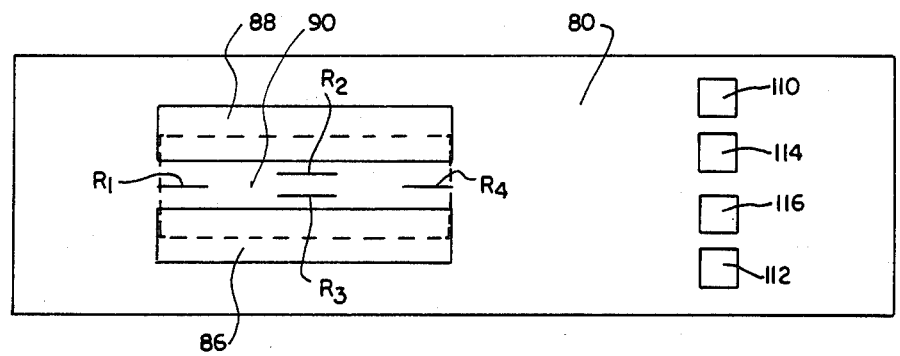
FIG. 8 is a plan view showing the non-recessed face of the element in FIGS. 5 and 6.

By constructing membrane beam 90 in the manner discussed above, the lateral deformation of the beam in response to pressure exerted thereon is far less than the longitudinal deformation. Moreover, the lateral deformation is essential negligible since the membrane beam behaves as a free beam having both ends fixed. This longitudinal deformation is sensed by four piezoelectric resistors $R_1$, $R_2$, $R_3$ and $R_4$ which may be formed, as by diffusion or ion implantation, in the membrane beam face 80. As is seen in FIG. 8, each of the resistors is a thin elongated element having a length that may well be greater than the width s of the beam but each is oriented so as to extend parallel to the longitudinal side edges of the membrane beam. None of the resistors is oriented transversely to the side edges and, hence, the width of the membrane beam may be quite narrow, permitting inclusion within catheters and needles of the smaller diameters.

Figure 9:
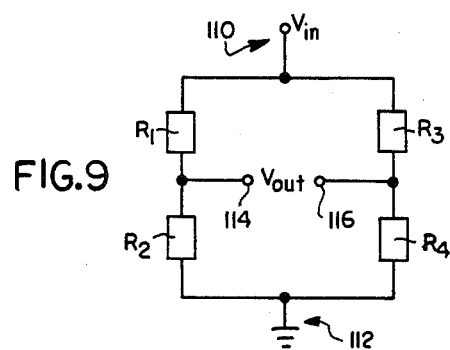
FIG. 9 is a schematic illustration of the resistors herein connected in a Wheatstone bridge arrangement.

The resistors are oriented as shown in FIG. 8 and are electrically interconnected to form a Wheatstone bridge, as is indicated in FIG. 9. The resistors are electrically interconnected, as by diffusion techniques or metal interconnects known in the art, with four bonding pads serving as terminal points 110, 112, 114 and 116. These terminal points are also schematically illustrated in FIG. 9. Thus, an input voltage $V_{in}$ may be connected across terminals 110 and 112, (the later being connected to electrical ground externally of the catheter) and an output voltage $V_{out}$ may be taken between terminals 114 and 116. Variations in the output voltage detected by the detector circuitry may be recorded or visually presented, as with meter 20.

In assembly, as illustrated in FIG. 2, the bonding pads 110-116 are individually connected to respective ones of the conductors 72 on the tape 60. These conductors, in turn, are individually connected to conductors 74 which extend through the lumen of catheter 110 to the power supply and detector circuit 18. In operation, when pressure is applied to the membrane beam resistors $R_2$ and $R_3$ and may be subject to tension forces, while resistors $R_1$ and $R_4$ are subject to compression forces and vice versa, depending upon whether the applied pressure is greater or less than atmospheric pressure.

Figure 10:
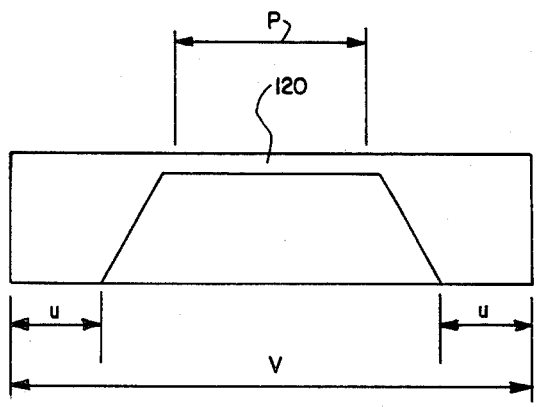
FIG. 10 is a view similar to FIG. 6 but showing a prior art element having large cross sectional dimensions; and, FIG. 11 is a view of the element of the present invention for comparison with FIG. 10 and exhibiting smaller cross sectional dimensions.
Figure 11:
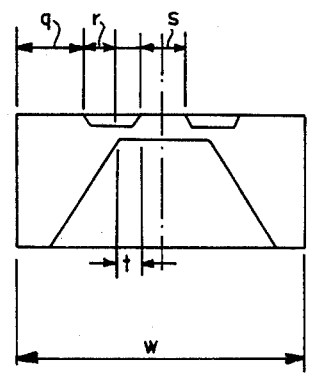

Reference is now made to FIGS. 9 and 10 which provide a comparative analysis of a prior art (FIG. 9) pressure-responsive membrane with that of the embodiment of the present invention (FIG. 10). Typically in the prior, as is viewed in FIG. 9, the width of a semiconductor block of which the membrane is formed is of a substantial width V, on the order of 1.2 millimeters. Similarly, width p of a membrane 120 formed in the semiconductor block may be on the order of 500 micrometers. The dimension u in the prior art device shown in FIG. 9 is relevant in connection with providing sufficient surface area for achieving adequate bonding strength in the event that the pressure-responsive element is attached to a support. This dimension may, for example, correspond with dimension q of the device in accordance with the present invention, as shown in FIG. 10.

The dimensions employed in the prior art device of FIG. 9 contrast drastically with the width dimensions of a device constructed in accordance with the present invention as is shown in FIG. 10. Here, the width dimension q may be on the order of 100 micrometers, the dimension r may be on the order of 25 micrometers, the dimension t may be on the order of 50 micrometers, and the width s of the membrane beam may be on the order of 100 micrometers. Consequently, then, the total width w of the device, as constructed in accordance with the invention, may be on the order of 450 micrometers, which is considerably less than the width v (1.2 micrometers) of the prior art pressure-responsive element shown in FIG. 10).

A comparison between the responsiveness of a prior art pressure-responsive element having a total width of 1.2 mm and that of a pressure-responsive element according to the invention having a total width of 0.7 mm was made by measuring experiments. The responsiveness s of the prior art pressure-responsive element appeared to be 15 $\mu V/V/mm$ Hg and of the pressure-responsive element according to the invention s=5 $\mu V/V/mm$ Hg. Unit $\mu V$ relates to the potential difference $\Delta V$ measured across the branches of the Wheatstone bridge, unit V to the excitation voltage $V_{bridge}$ of the Wheatstone bridge, and unit mm Hg to the pressure difference $\Delta p$ across the membrane.

In summation, by constructing a pressure-responsive element in accordance with the present invention, the cross sectional width dimensions may be considerably reduced from that of the prior art, while achieving sufficient pressure responsiveness so that the element may be employed in catheters and needles having reduced inner diameters. It is to be appreciated that various modifications may be made without departing from the spirit and scope of the invention as defined by the appended claims.

Having described a preferred embodiment, the following is claimed:

1. A catheter tip pressure transducer for use in measuring fluid pressure within a living body, comprising;

a tubular housing having a pressure inlet aperture formed therein;

a semiconductor block carried within said housing and having first and second oppositely directed major surfaces, one of which faces said inlet aperture;

said first surface having a recess defined therein such that the floor of said recess and said second surface define therebetween a relatively thin rectangular portion having a length l, a width b and a thickness d;

said second surface having a pair of longitudinally extending grooves, each of a length l, defined therein in registry with the longitudinal side edges of said rectangular portion so as to define therebetween an elongated longitudinally extending rectangular membrane beam of a length l, a width s which is less than width b and a thickness d with said membrane beam acting as a free beam supported in the longitudinal direction at its opposite ends by and integral with said semiconductor block and relatively unsupported in the lateral direction such that applied pressure results mainly in longitudinal deformations of said membrane beam; and strain gauge means carried by said membrane beam and responsive to said longitudinal deformation thereof for providing an output indication representative of said applied pressure.

2. A transducer as set forth in claim 1, wherein said pair of grooves extend through said rectangular portion defining longitudinally extending slots bordering the longitudinally extending side edges of said membrane beam, a coating layer overlying said slots on said second surface and adhering thereto so as to permit a pressure differential across said first and second surfaces.

3. A transducer as set forth in claim 2, wherein said coating layer is of a polymer material.

4. A transducer as set forth in claim 1 wherein said grooves are each rectangular in shape having a width c and a depth on the order of ½ d, said grooves overlap the corresponding longitudinal edges of said rectangular portion on either side thereof by a distance of approximately ½ c.

5. A transducer as set forth in claim 4 wherein the width s of said membrane beam is on the order of width b−width c.

6. A transducer as set forth in claim 1 wherein said strain gauge means includes four elongated piezoelectric resistors connected together to define a Wheatstone bridge circuit and with each resistor being located on said membrane beam and oriented so as to extend parallel to the longitudinal side edges thereof.

7. A transducer as set forth in claim 6, including a rigid support member of insulating material located in said housing, said semiconductor block being rigidly secured to said support member.

8. A transducer as set forth in claim 1, wherein said first surface faces said inlet aperture and said strain gauge means are located on said second surface.

* * * * *